(12) United States Patent
Maeda et al.

(10) Patent No.: US 11,464,866 B2
(45) Date of Patent: Oct. 11, 2022

(54) PHARMACEUTICAL COMPOSITION CONTAINING MACROMOLECULAR DRUG

(71) Applicant: BIODYNAMIC RESEARCH FOUNDATION, Kumamoto (JP)

(72) Inventors: Hiroshi Maeda, Kumamoto (JP); Jun Fang, Kumamoto (JP)

(73) Assignee: BIODYNAMIC RESEARCH FOUNDATION, Kumamoto (JP)

( * ) Notice: Subject to any disclaimer, the term of this patent is extended or adjusted under 35 U.S.C. 154(b) by 73 days.

(21) Appl. No.: 16/098,507

(22) PCT Filed: May 2, 2017

(86) PCT No.: PCT/JP2017/017288
§ 371 (c)(1),
(2) Date: Nov. 2, 2018

(87) PCT Pub. No.: WO2017/191843
PCT Pub. Date: Nov. 9, 2017

(65) Prior Publication Data
US 2019/0142955 A1    May 16, 2019

(30) Foreign Application Priority Data
May 6, 2016  (JP) .............................. JP2016-093407

(51) Int. Cl.
| | | |
|---|---|---|
| *A61K 47/12* | (2006.01) | |
| *A61K 31/351* | (2006.01) | |
| *A61K 47/18* | (2017.01) | |
| *A61K 47/50* | (2017.01) | |
| *A61K 9/08* | (2006.01) | |
| *A61K 47/58* | (2017.01) | |
| *A61P 35/00* | (2006.01) | |
| *A61K 9/00* | (2006.01) | |
| *A61K 47/02* | (2006.01) | |
| *A61K 47/32* | (2006.01) | |
| *A61K 47/60* | (2017.01) | |
| *A61K 47/10* | (2017.01) | |
| *A61K 47/24* | (2006.01) | |
| *A61K 47/26* | (2006.01) | |
| *A61K 47/36* | (2006.01) | |
| *A61K 47/42* | (2017.01) | |
| *A61K 31/555* | (2006.01) | |
| *A61K 9/14* | (2006.01) | |

(52) U.S. Cl.
CPC ............ *A61K 47/60* (2017.08); *A61K 9/0019* (2013.01); *A61K 9/08* (2013.01); *A61K 9/14* (2013.01); *A61K 31/351* (2013.01); *A61K 31/555* (2013.01); *A61K 47/02* (2013.01); *A61K 47/10* (2013.01); *A61K 47/12* (2013.01); *A61K 47/18* (2013.01); *A61K 47/183* (2013.01); *A61K 47/24* (2013.01); *A61K 47/26* (2013.01); *A61K 47/32* (2013.01); *A61K 47/36* (2013.01); *A61K 47/42* (2013.01); *A61K 47/50* (2017.08); *A61K 47/58* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 5,026,772 A | 6/1991 | Kobayashi et al. | |
| 5,217,705 A * | 6/1993 | Reno .................... | A61K 51/08 424/1.69 |
| 5,389,366 A | 2/1995 | Maeda et al. | |
| 6,280,991 B1 * | 8/2001 | Raines .................. | A61P 35/00 435/199 |
| 9,636,426 B2 * | 5/2017 | Maeda .................. | A61P 35/00 |
| 2003/0199090 A1 * | 10/2003 | Monahan ............ | A61K 48/0025 435/455 |
| 2007/0032422 A1 * | 2/2007 | Gulati ................. | A61K 31/282 424/85.4 |
| 2009/0297689 A1 * | 12/2009 | Edens .................. | A23L 33/00 426/656 |
| 2011/0112036 A1 | 5/2011 | Demeule et al. | |
| 2012/0296048 A1 | 11/2012 | Etrych et al. | |
| 2014/0294735 A1 | 10/2014 | Maeda et al. | |
| 2015/0283252 A1 | 10/2015 | Vadgama et al. | |
| 2016/0317672 A1 | 11/2016 | Maeda et al. | |
| 2017/0298190 A1 | 10/2017 | Fujita et al. | |
| 2018/0236091 A1 | 8/2018 | Aoki et al. | |

FOREIGN PATENT DOCUMENTS

| | | |
|---|---|---|
| JP | 64-85922 | 3/1989 |
| JP | 1-156925 | 6/1989 |
| JP | 2002-514210 | 5/2002 |
| JP | 2010-24170 | 2/2010 |
| JP | 2011-516587 | 5/2011 |
| JP | 2015-535238 | 12/2015 |
| WO | 98/042382 | 10/1998 |
| WO | 2011/072627 | 6/2011 |
| WO | 2013/035750 | 3/2013 |
| WO | 2015/076312 | 5/2015 |
| WO | 2016/103867 | 6/2016 |
| WO | 2017/038607 | 3/2017 |

OTHER PUBLICATIONS

Iyer et al., Drug Discovery Today vol. 11 No. 17/18. (Year: 2006).*
Bunker Physics Procedia vol. 34, pp. 24-33. (Year: 2012).*

(Continued)

*Primary Examiner* — Katherine Peebles
(74) *Attorney, Agent, or Firm* — Wenderoth, Lind & Ponack, L.L.P.

(57) ABSTRACT

The present invention provides a formulation having excellent solubility and/or stability of a macromolecular drug, and more specifically, a pharmaceutical composition containing a macromolecular drug, a dissolution-enhancing and/or stabilizing agent, and an aqueous solvent, wherein the dissolution-enhancing and/or stabilizing agent is at least one selected from the group consisting of (1) proteins, (2) synthetic polymers, (3) sugars or sugar alcohols, (4) inorganic salts, (5) amino acids, (6) phospholipids, (7) aliphatic alcohols, (8) medium-chain fatty acids, and (9) mucopolysaccharides.

10 Claims, 8 Drawing Sheets

(56) References Cited

OTHER PUBLICATIONS

Chassany et al. Cancer Chemother Pharmacol (1996) 38: 571-573. (Year: 1996).*

Extended European Search Report dated Nov. 11, 2019 in corresponding European Patent Application No. 17792775.3.

Fang et al., "HSP32 (HO-1) inhibitor, copoly(styrene-maleic acid)-zinc protoporphyrin IX a water-soluble micelle as anticancer agent: In vitro and in vivo anticancer effect", European Journal of Pharmaceutics and Biopharmaceutics, 2012, vol. 81, pp. 540-547.

English Translation of International Preliminary Report on Patentability dated Nov. 6, 2018 in International (PCT) Application No. PCT/JP2017/017288.

Nakamma et al., "Two Step Mechanisms of Tumor Selective Delivery of N-(2-Hydroxypropyl) Methacrylamide Copolymer Conjugated with Pirarubicin via an Acid-Cleavable Linkage", Journal of Controlled Release, vol. 174, pp. 81-87 (2014), Cited in CA.

Nakamura et al., "Micelles of Zinc Protoporphyrin Conjugated to N-(2-Hydroxypropyl) Methacrylamide (HPMA) Copolymer for Imaging and Light-induced Antitumor Effects In Vivo", Journal of Controlled Release, vol. 165, pp. 191-198 (2013), Cited in CA.

Tsukigawa et al., "Synthesis and Therapeutic Effect of Styrene-Maleic Acid Copolymer-Conjugated Pirarubicin", Cancer Science, vol. 106:3, pp. 270-278 (2015), Cited in CA.

Hiroshi et al., "Enhancement of Anticancer-drug Delivery and Therapeutic Effect by Augmentation of EPR Effect of Tumor Lesion Using Nitroglycerin Ointment", Drug Delivery System, vol. 24:3, p. 319 (2009), with English Translation, Cited in CA.

Stuehr, Dennis J., "Arginine Metabolism: Enzymology, Nutrition, and Clinical Significance", The Journal of Nutrition, vol. 134, pp. 2748s-2751s (2004), Cited in CA.

King, Bruce S., "Nitric Oxide Production from Hydroxyurea", Free Radical Biology & Medicine, vol. 37:6, pp. 737-744 (2004), Cited in CA.

Sueyoshi et al., "Study of N-Nitroso Compounds which have NO-Release Ability", Bulletin National Institutes of Health Science, vol. 115, pp. 40-48 (1997).

Khormaee et al., "Endosomolytic Anionic Polymer for the Cytoplasmic Delivery of siRNAs in Localized In Vivo Applications", Advanced Functional Materials, vol. 23, pp. 565-574 (2013).

Matsumura et al., "A New Concept for Macromolecular Therapeutics in Cancer Chemotherapy: Mechanism of Tumoritropic Accumulation of Proteins and the Antitumor Agent Smancs[1]", Cancer Research, vol. 46, pp. 6387-6392 (1986), Cited in Specification.

Maeda, Hiroshi, "The Enhanced Permeability and Retention (EPR) Effect in Tumor Vasculature: The Key Role of Tumor-Selective Macromolecular Drug Targeting", Advanced Enzyme Regulation, vol. 41, pp. 189-207 (2001), Cited in Specification.

Maeda et al., "The EPR Effect for Macromolecular Drug Delivery to Solid Tumors: Improvement of Tumor Uptake, Lowering of Systemic Toxicity, and Distinct Tumor Imaging in Vivo", Advanced Drug Delivery Reviews, vol. 65, pp. 71-79 (2013), Cited in Specification.

Maeda, Hiroshi, "Vascular Permeability in Cancer and Infection as Related to Macromolecular Drug Delivery, with Emphasis on the EPR Effe . . .", Proceedings of the Japan Academy SerB Physical and Biological Sciences, vol. 88, pp. 53-71 (2012), Cited in Specification.

Seki et al., "Enhanced Delivery of Macromolecular Antitumor Drugs to Tumors by Nitroglycerin Application", Cancer Science, vol. 100, pp. 2426-2430 (2009), Cited in Specification.

Fang et al., "The EPR Effect: Unique Features of Tumor Blood Vessels for Drug Delivery, Factors Involved, and Limitations and Augmentation of the Effect", Advanced Drug Delivery Reviews, vol. 63, pp. 136-151 (2011), Cited in Specification.

Maeda, Hiroshi, "Macromolecular Therapeutics in Cancer Treatment: The EPR Effect and Beyond", Journal of Controlled Release, vol. 164, pp. 138-144 (2012), Cited in Specification.

Fang, et al., "Water Soluble PEG-conjugate of Xanthine Oxidase Inhibitor, PEG-AHPP Micelles, as a Novel Therapeutic for ROS Related Inflammatory Bowel Diseases", Journal of Controlled Release, vol. 223, pp. 188-196 (2016), Cited in Specification.

Maeda and Khatami, "Analyses of Repeated Failures in Cancer Therapy for Solid Tumors: Poor Tumor-Selective Drug Delivery, Low Therapeutic Efficacy and Unsustainable Costs", Clinical and Translational Medicine, vol. 7:11, pp. 1-20 (2018).

Islam et al., "HPMA Copolymer Conjugate with Pirambicin: in Vitro and Ex Vivo Stability and Drug Release Study", International Journal of Pharmaceutics, vol. 536, pp. 108-115 (2018).

* cited by examiner

[Figure 1]
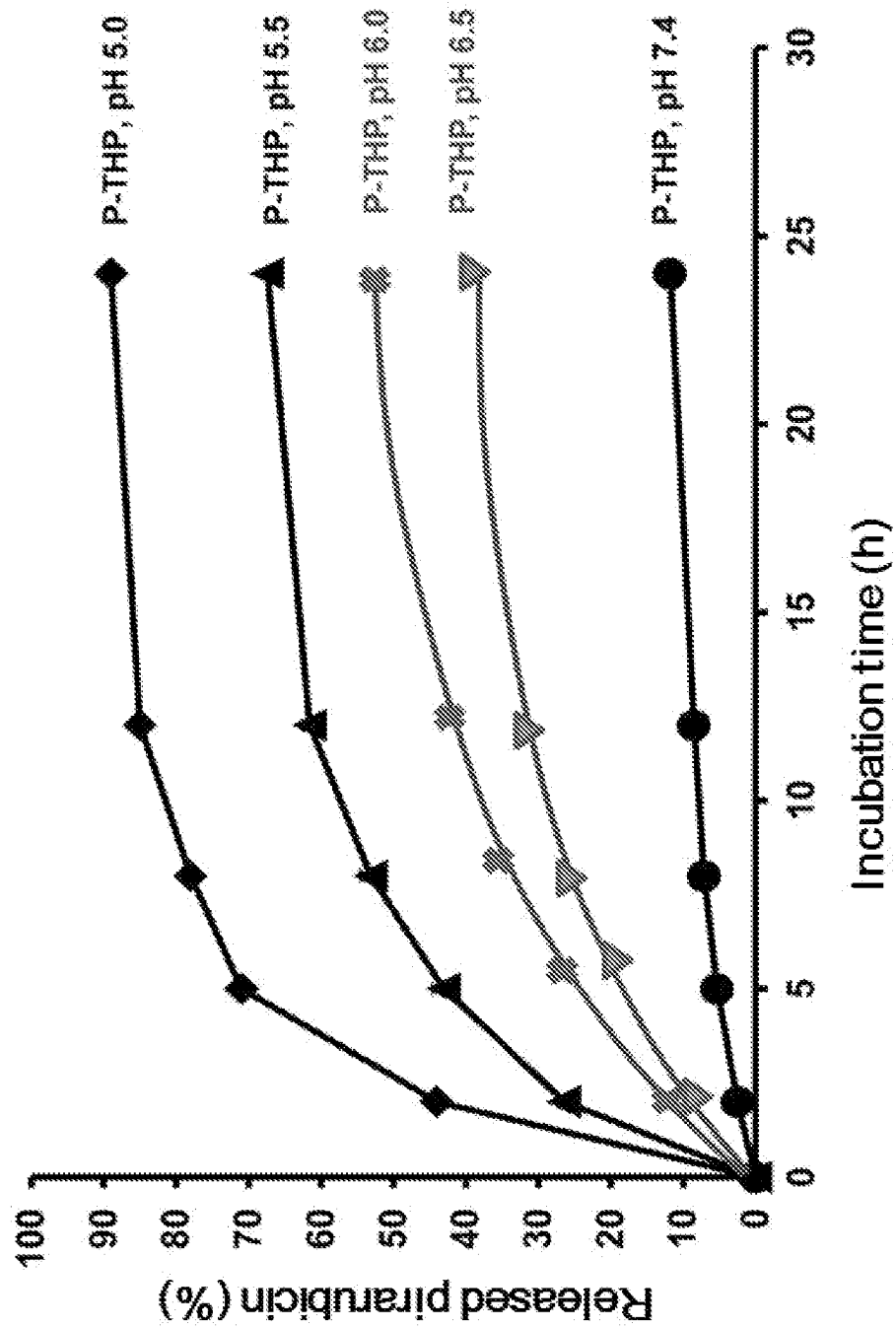

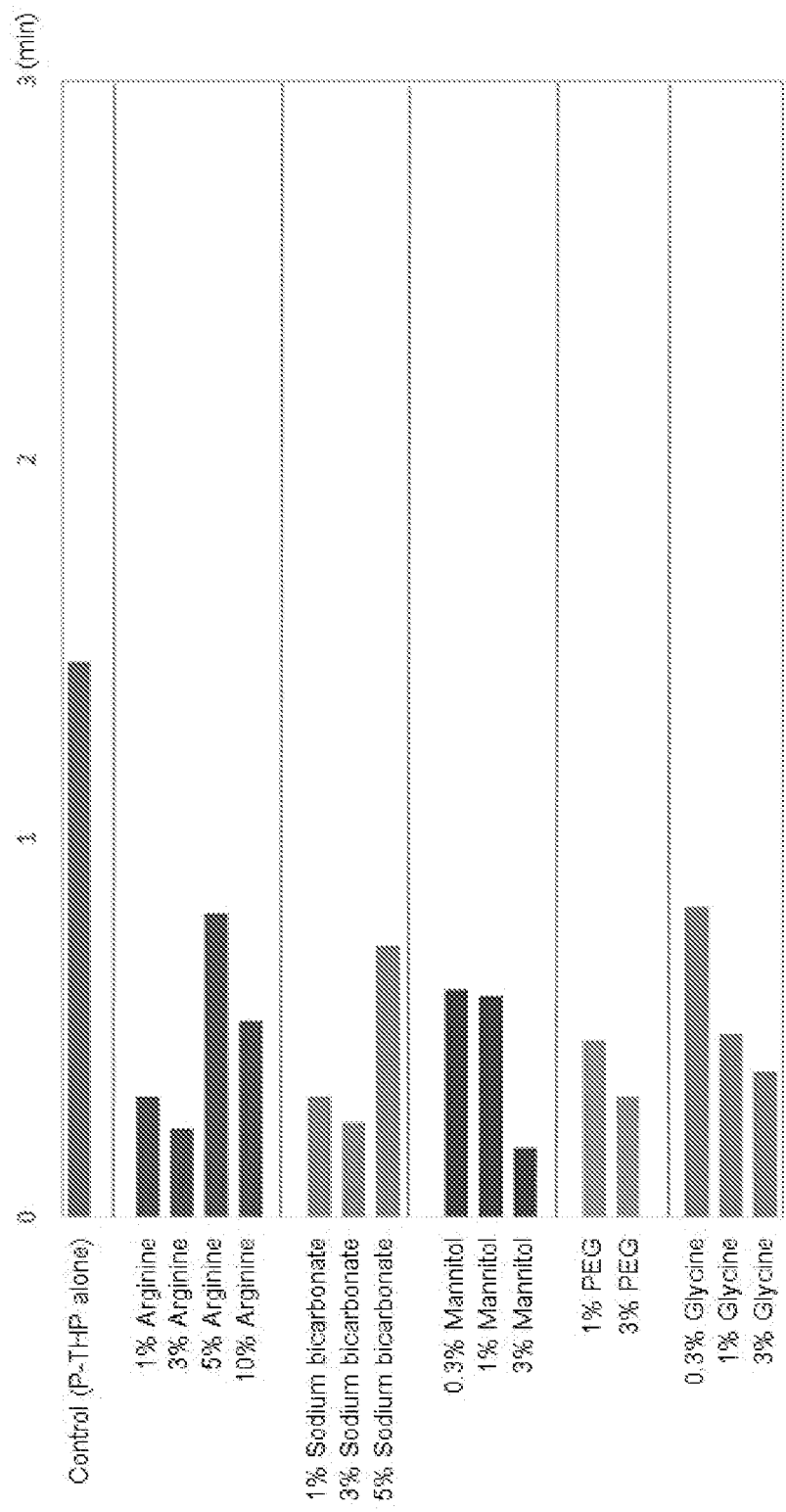

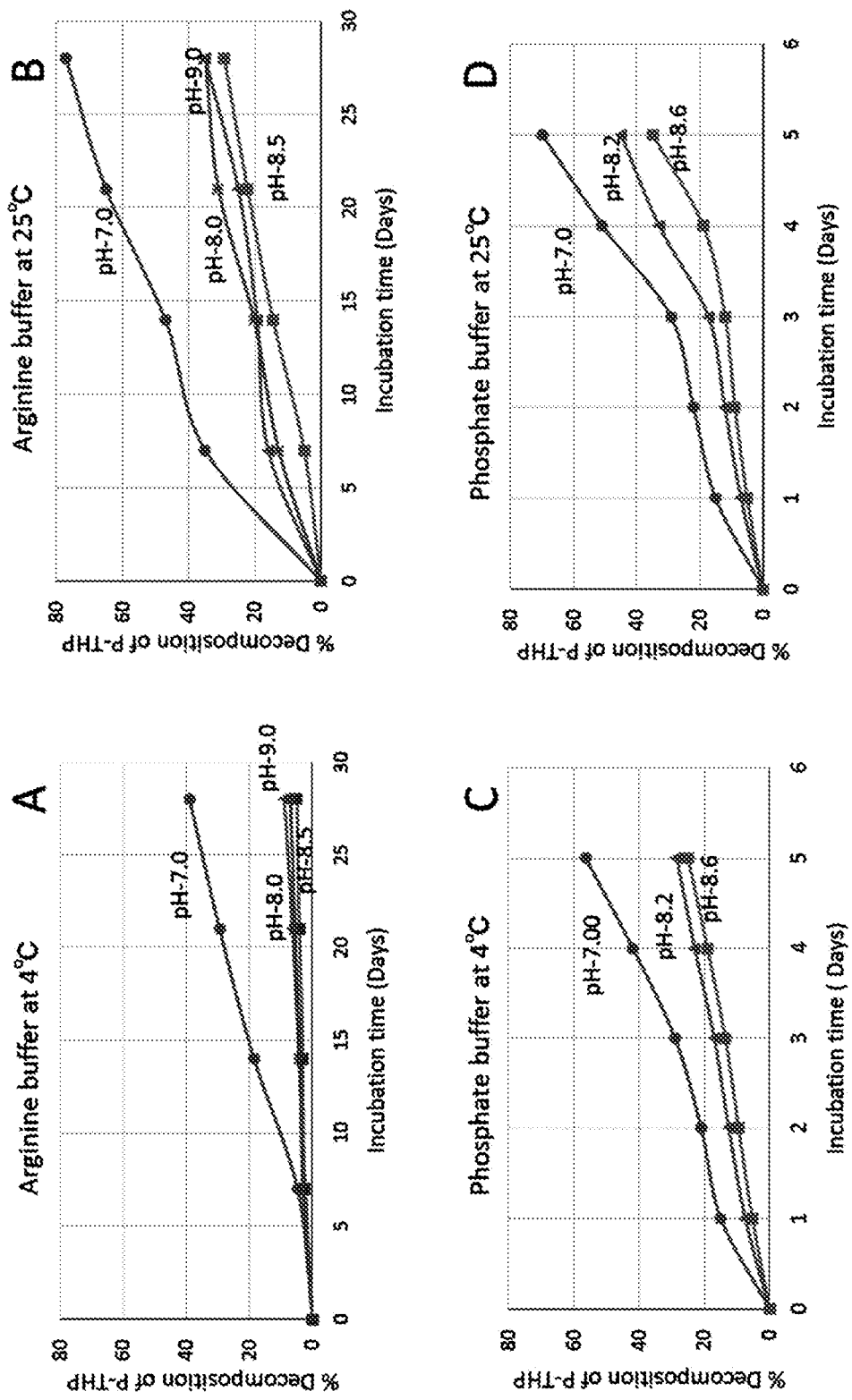
[Figure 3-1]

[Figure 3-2]
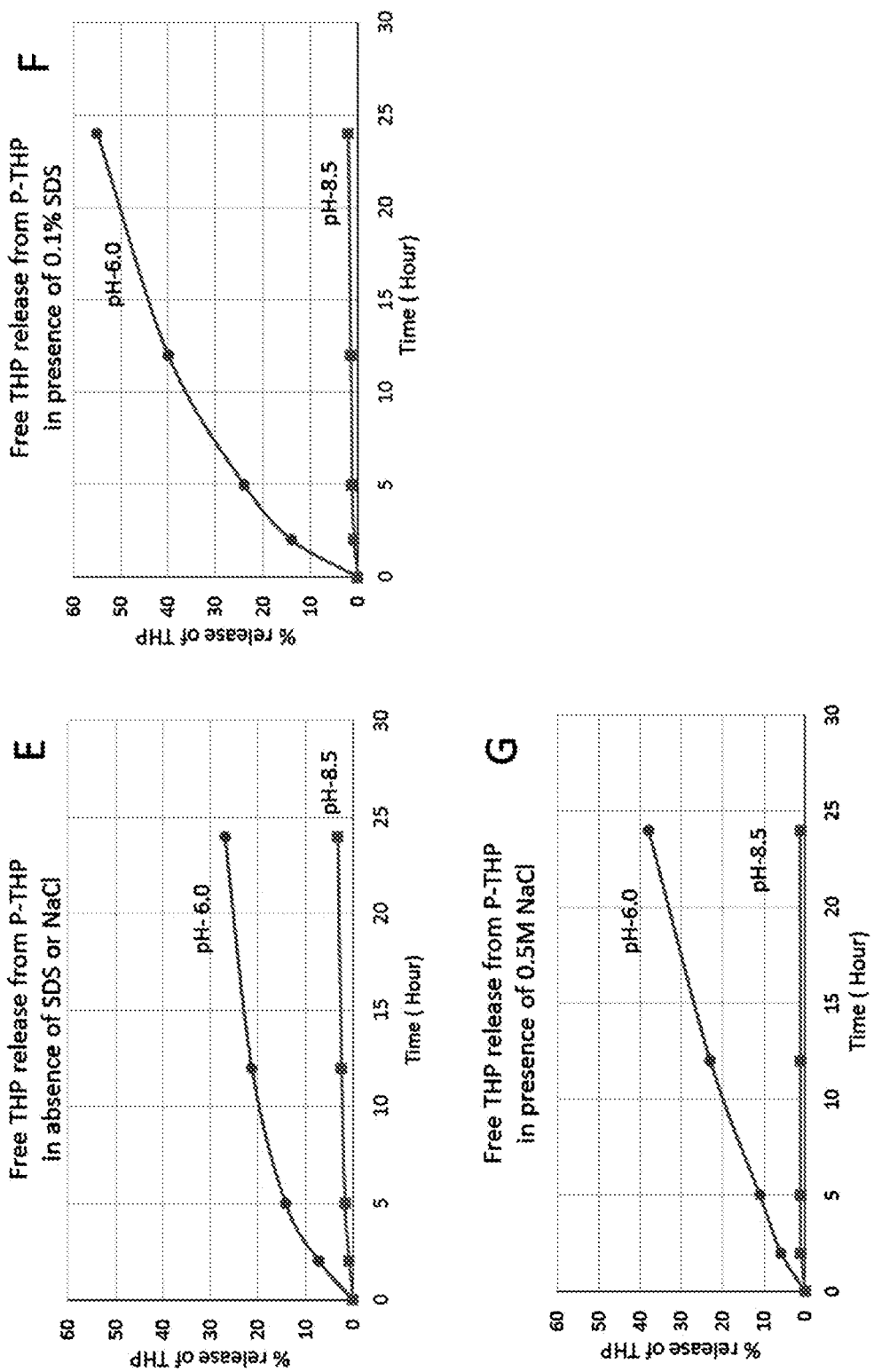

[Figure 4]
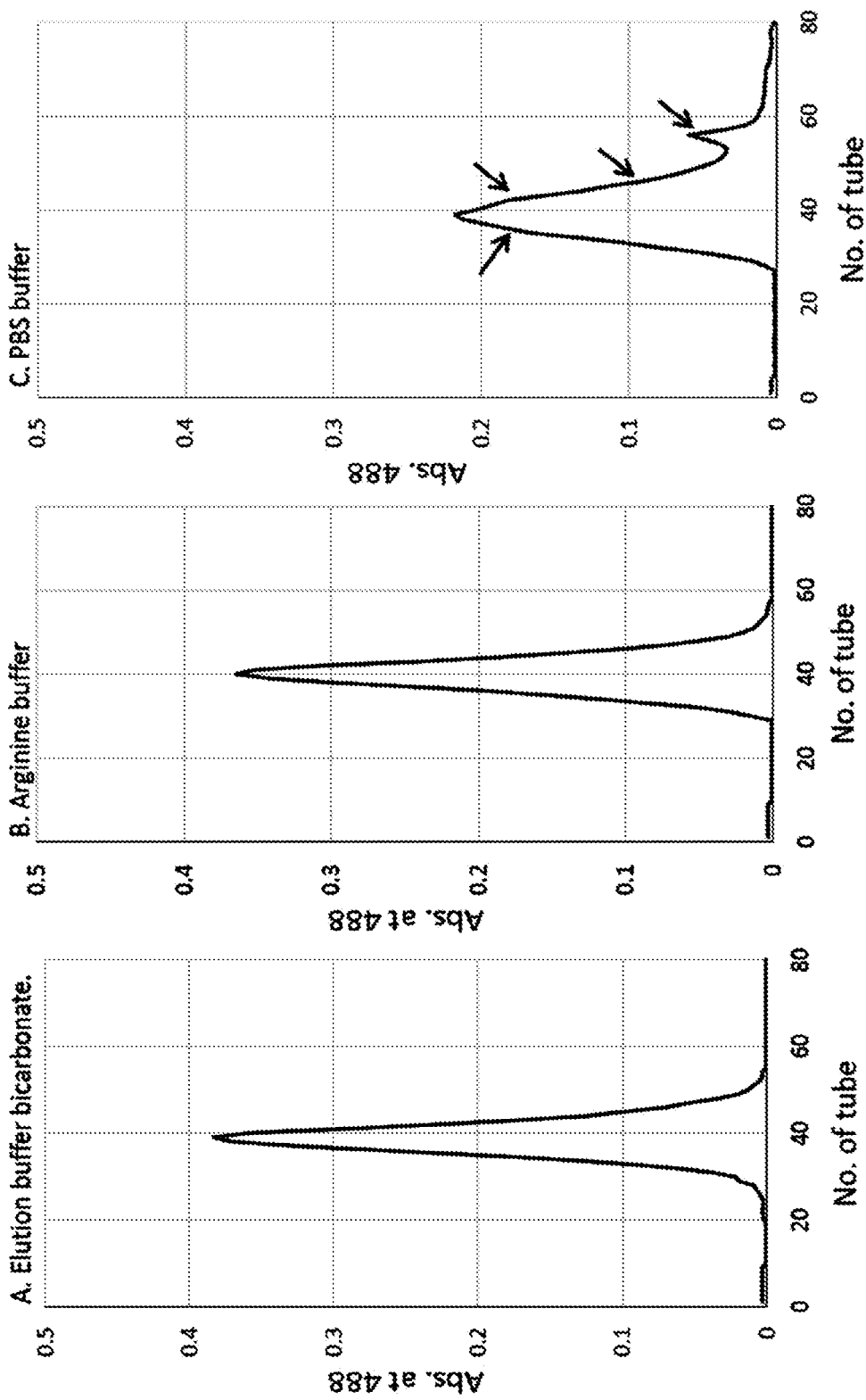

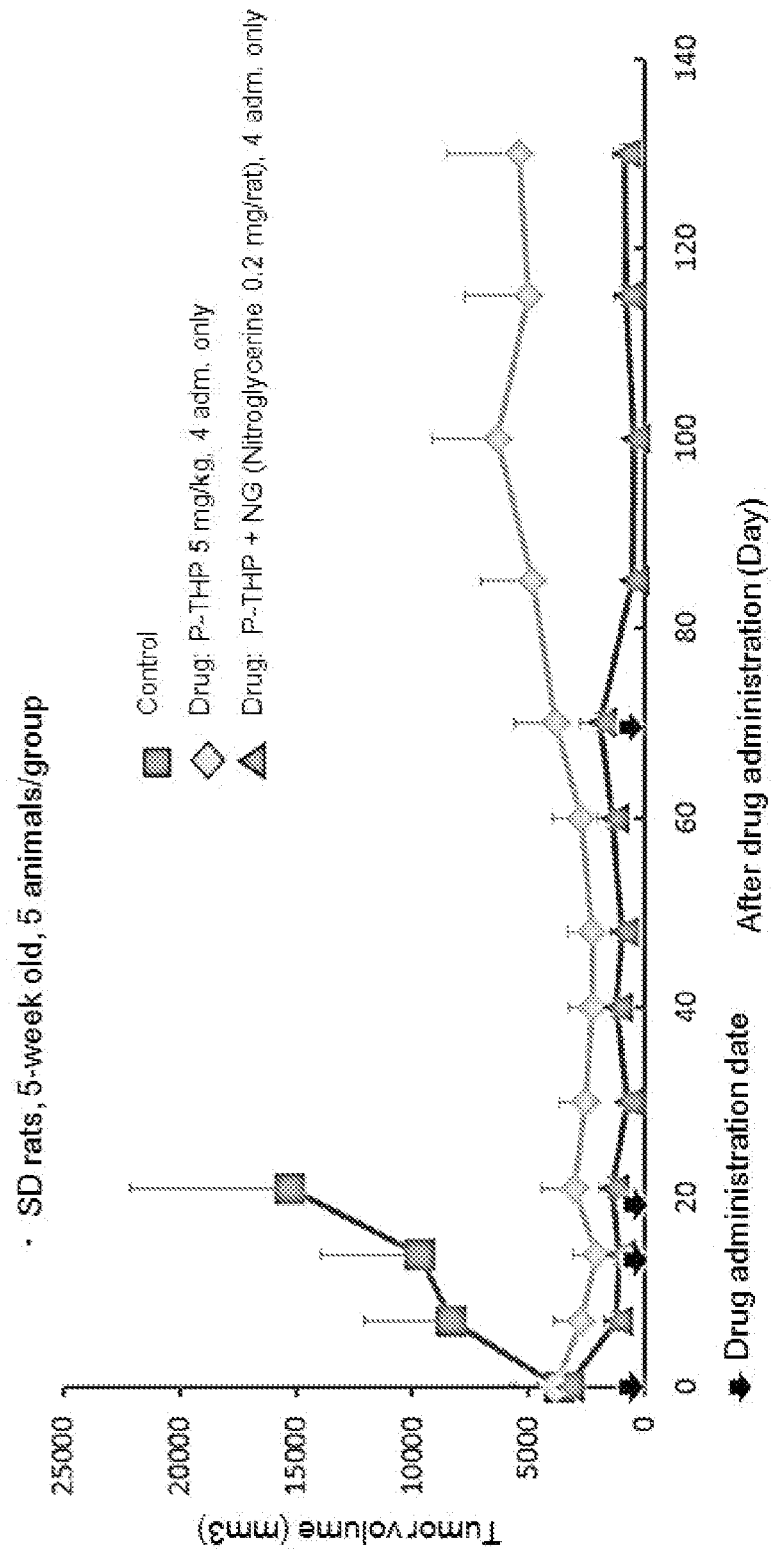
[Figure 5]

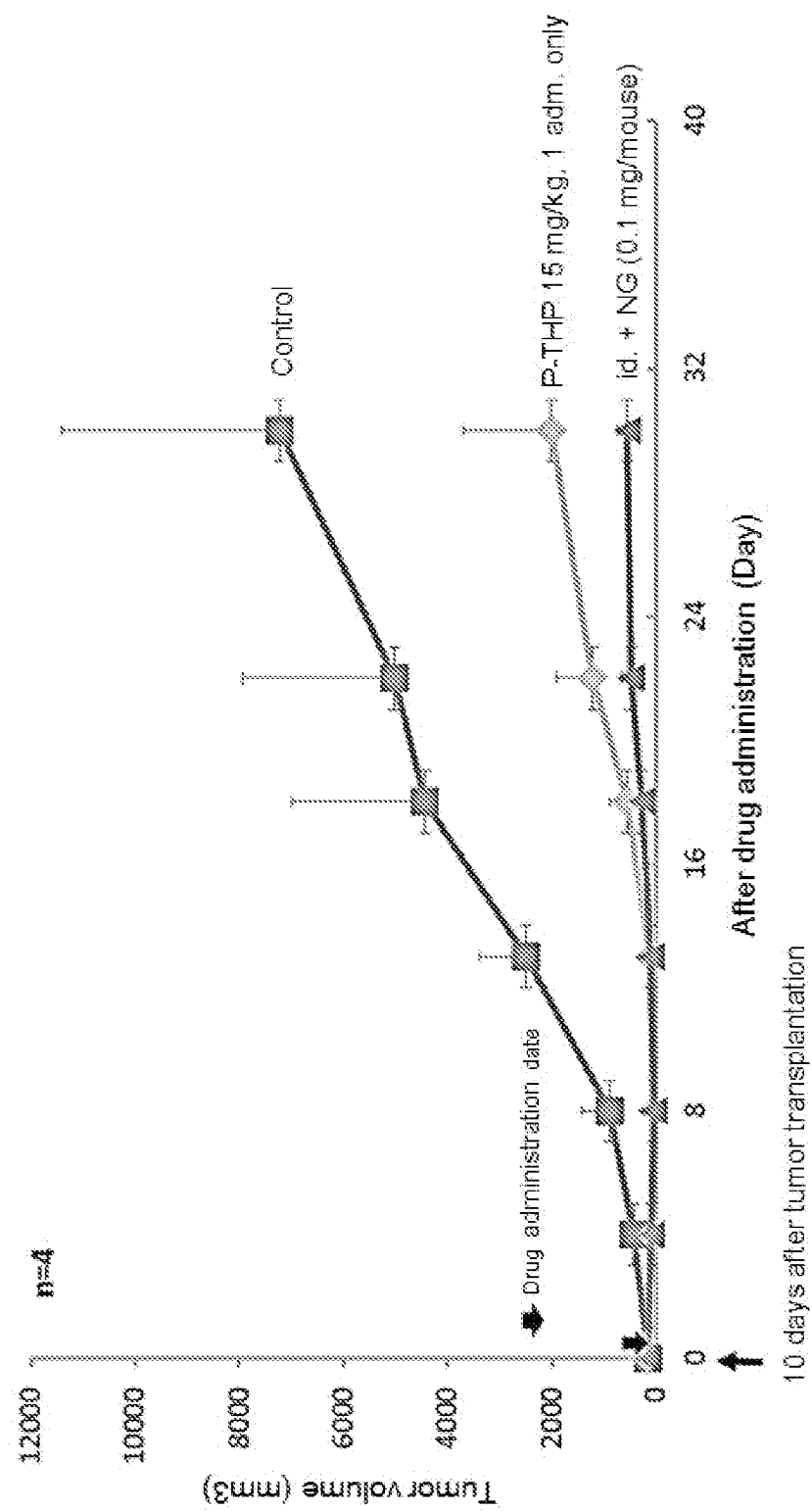

[Figure 7]
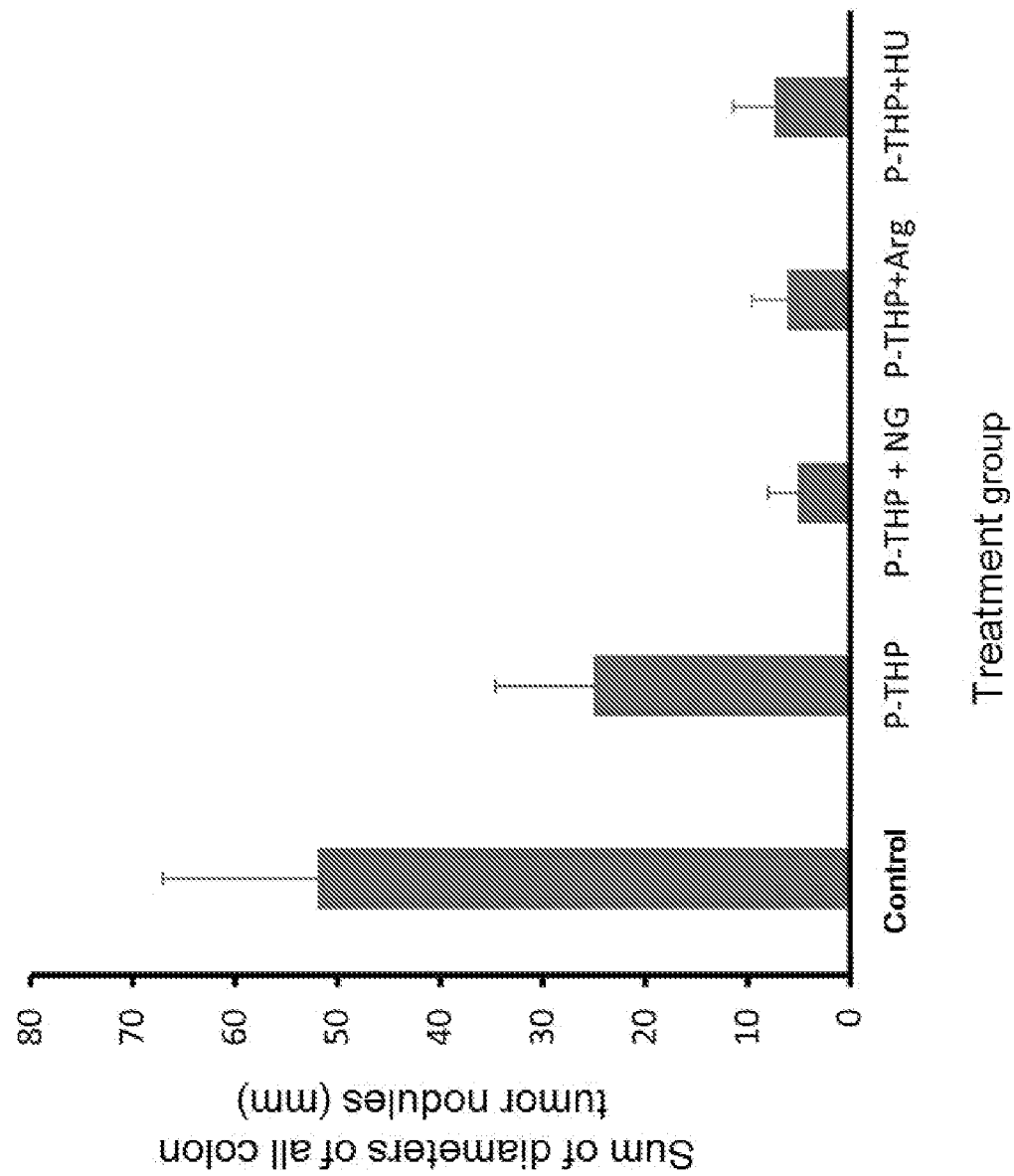

PHARMACEUTICAL COMPOSITION CONTAINING MACROMOLECULAR DRUG

TECHNICAL FIELD

The present application is filed claiming the priority of the Japanese Patent Application No. 2016-93407, the entire contents of which are herein incorporated by reference.

The present invention relates to a pharmaceutical composition containing a macromolecular drug, particularly an injection, and a method for producing the same.

BACKGROUND ART

Many conventional carcinostatic agents (also referred to as antitumor agents or anticancer agents) have a molecular weight of 1500 or less. Most of such agents diffuse uniformly in the body, and thus cause side effects on normal organs and show poor selective toxicity to tumors. It is therefore difficult to use these carcinostatic agents in an increased dosage with the expectation of stronger effects, because the side effects thereof are increased.

In contrast to the above conventional general theory, the present inventors made a drug into a macromolecular form by, for example, binding a biocompatible polymer to a carcinostatic agent, and then discovered the phenomenon that said drug shows a suppressed excretion (disappearance) from the blood through the kidney and a prolonged blood retention and leaks more selectively to the extravascular space at tumor sites owing to the enhanced vascular permeability (leakiness) and retention effect expressed in the solid tumor. The present inventors reported this phenomenon as an EPR (enhanced permeability and retention) effect (Non-Patent Documents 1 to 4) as a general concept.

The present inventors developed novel macromolecule-bound carcinostatic agents of pirarubicin (THP), for example, a polyhydroxypropylmethacrylamide (HPMA)-bound THP (P-THP) and a styrene-maleic acid copolymer (SMA)-bound THP (SMA-THP), and also macromolecule-bound conjugates of Zn-protoporphyrin (ZnPP) (P-ZnPP and SMA-ZnPP) (Patent documents 1 to 2). On the other hand, the present inventors revealed various pharmacological factors involved in the enhancement of the EPR effect. Examples of the factor include bradykinin, nitric oxide (NO), carbon monoxide, substances promoting their production, and ACE (angiotensin-converting enzyme) inhibitors (Non-Patent Documents 5 to 8). NO-releasing agents involved in the NO concentration of tumor sites or ACE inhibitors enhance the EPR effect in tumors by 2 to 3 times and also the tumor delivery of the above macromolecular drugs by 2 to 3 times (Non-Patent Documents 5 to 8).

CITATION LIST

Patent Documents

Patent Document 1: WO 2013/035750
Patent Document 2: WO 2015/076312

Non-Patent Documents

Non-Patent Document 1: Y. Matsumura & H. Maeda, Cancer Res. (1986) 46, p. 6387-6392.
Non-Patent Document 2: H. Maeda, Adv. in Enzyme Regulation (2001) 41, p. 189-207.
Non-Patent Document 3: H. Maeda et al, Adv. Drug Deliv. Res (2013) 65, p. 71-79.
Non-Patent Document 4: Proc. Japan Acad. Ser. B (2012) 88, p. 53-71.
Non-Patent Document 5: T. Seki et al, Cancer Sci. (2009) 100, p. 2426-2430.
Non-Patent Document 6: J. Fang et al, ADD Review (2011) 63, p. 136-151
Non-Patent Document 7: H. Maeda, J. Control Release (2012) 164, p. 138-144
Non-Patent Document 8: Fang et al, J. Control Release (2016) 223, p. 188-196

SUMMARY OF INVENTION

Technical Problem

Many macromolecular drugs show a relatively uniform molecular weight distribution due to particularly the formation of more complicated high order structure, or molecular interaction thereby. However, it may be difficult to maintain the proper high order structure in solution because of the formation of further complexes caused by strong interaction between the macromolecules, the inhibition of the complicated interaction between the side chain molecules thereof, or the like. The macromolecular drug molecules may also tend to associate with each other and form insoluble aggregates. Therefore, there are problems with the macromolecular drugs, such as low stability. Also, the macromolecules are often too strongly associated each other and thus do not disperse or dissolve in uniform aqueous solution.

Stability of molecular integrity is an especially important problem in micelle or liposome formulations, which are in the form of a macromolecule by intermolecular association. For example, if a micelle or liposome preparation has a problem with stability in a solution, there is a risk that the micelle-forming ability is lost or the encapsulated drug is released (liberated).

It is therefore desired to overcome a problem with solubility or instability in a solution of macromolecular drugs in order to improve the stability of such macromolecules in vivo and to maintain the tumor selectivity due to the EPR effect of the drugs. It is also important to enhance the EPR effect of these macromolecular drugs upon intravenous administration, because enhancement of EPR effect can result in increased anticancer effects and reduced side effects by the drugs.

In addition, many macromolecular drugs such as micelle formulations or the so-called nanomedicines have poor solubility, and this causes a problem in the bedside when a powder (solid) thereof is dissolved in an aqueous solvent to use it as an injection or the like.

Solution to Problem

As a result of intensive studies in view of the above problems, the present inventors have found that when a macromolecular drug (e.g., P-THP) is dissolved in an aqueous solvent to prepare an injection solution, the addition of a specific dissolution-enhancing and/or stabilizing agent to the solvent makes it possible to reduce the dissolution time of the macromolecular drug in the aqueous solvent, i.e., to promote the dissolution of the macromolecular drug, and to stabilize an ester bond, a hydrazone bond or a specific amide bond in the drug molecule in an aqueous solution, and also the addition of a specific dissolution-enhancing and/or stabilizing agent (e.g., arginine which is a substrate of NO synthase in vivo) makes it possible to enhance the EPR effect, etc. of the macromolecular drug as well as the above promoted dissolution and stabilization, thereby reaching to the present invention.

Accordingly, the present invention includes the followings.

[1] A pharmaceutical composition comprising a macromolecular drug, a dissolution-enhancing and/or stabilizing agent, and an aqueous solvent, wherein the dissolution-enhancing and/or stabilizing agent is at least one selected from the group consisting of
(1) proteins,
(2) synthetic polymers,
(3) sugars or sugar alcohols,
(4) inorganic salts,
(5) amino acids,
(6) phospholipids,
(7) aliphatic alcohols,
(8) medium-chain fatty acids, and
(9) mucopolysaccharides.

[2] The pharmaceutical composition according to [1], which has a pH of 7.0 to 8.0.

[3] The pharmaceutical composition according to [1] or [2], which is an injection.

[4] The pharmaceutical composition according to any one of [1] to [3], wherein the macromolecular drug is at least one selected from the group consisting of P-THP, P-ZnPP, SMA-THP, SMA-ZnPP, PEG-THP, and PEG-ZnPP.

[5] The pharmaceutical composition according to any one of [1] to [4], wherein the bond between the drug and the polymer in the macromolecular drug is at least one selected from the group consisting of an amide bond, an ester bond, a hydrazone bond, and a bond through Schiff base.

[6] The pharmaceutical composition according to [5], wherein the bond between the drug and the polymer in the macromolecular drug is a hydrazone bond.

[7] The pharmaceutical composition according to any one of [1] to [6], wherein the dissolution-enhancing and/or stabilizing agent is at least one selected from the group consisting of arginine and citrulline.

[8] The pharmaceutical composition according to any one of [1] to [7], which further comprises an EPR and/or antitumor effect enhancer.

[9] The pharmaceutical composition according to any one of [1] to [8], which is for carcinostatic or anti-tumor effect.

[10] A method for producing the pharmaceutical composition according to any one of [1] to [9], which comprises mixing the macromolecular drug, the dissolution-enhancing and/or stabilizing agent, and the aqueous solvent.

[11] A pharmaceutical composition comprising a macromolecular drug, and a dissolution-enhancing and/or stabilizing agent, wherein the dissolution-enhancing and/or stabilizing agent is at least one selected from the group consisting of
(1) proteins,
(2) synthetic polymers,
(3) sugars or sugar alcohols,
(4) inorganic salts,
(5) amino acids,
(6) phospholipids,
(7) aliphatic alcohols,
(8) medium-chain fatty acids, and
(9) mucopolysaccharides.

[12] The pharmaceutical composition according to [11], which further comprises an EPR and/or antitumor effect enhancer.

[13] A pharmaceutical composition comprising a macromolecular drug, and an EPR and/or antitumor effect enhancer, wherein the EPR and/or antitumor effect enhancer is at least one selected from the group consisting of
(1) nitroglycerin,
(2) arginine,
(3) hydroxyurea, and
(4) nitrosourea.

[14] The pharmaceutical composition according to [13], which further comprises a dissolution-enhancing and/or stabilizing agent.

[15] A method for enhancing dissolution and/or stabilizing a macromolecular drug, which comprises mixing the macromolecular drug with at least one dissolution-enhancing and/or stabilizing agent selected from the group consisting of
(1) proteins,
(2) synthetic polymers,
(3) sugars or sugar alcohols,
(4) inorganic salts,
(5) amino acids,
(6) phospholipids,
(7) aliphatic alcohols,
(8) medium-chain fatty acids, and
(9) mucopolysaccharides.

Effect of Invention

According to the pharmaceutical composition of the present invention, it is possible to markedly reduce the dissolution time of a macromolecular drug (e.g., P-THP) in an aqueous solvent, i.e., to promote dissolution of the macromolecular drug, and to significantly improve the stability of the macromolecular drug in a solution by a specific dissolution-enhancing and/or stabilizing agent. Furthermore, according to the present invention, it is possible to remarkably enhance the EPR effect, thus tumor delivery, anti-tumor effect, etc. of a macromolecular drug, in addition to the above effects, by a specific dissolution-enhancing and/or stabilizing agents.

Accordingly, when, for example, an anti-tumor agent is used as the drug, the pharmaceutical composition of the present invention becomes better antitumor pharmaceutical composition. When, for example, a fluorescent molecule is used as the drug, it is possible to promote the enhancement of EPR effect of the molecule to obtain a higher tumor accumulation thereof by administering it in the form of the present composition, compared with when administering it in the form of a single drug. The pharmaceutical composition of the present invention is thus very useful as a fluorescent probe for tumor.

According to the present invention, it is possible to provide, as a dosage form of a macromolecular drug, an injection easily dissolved in a specific aqueous solution or alike when used, which has an improved stability and shows an enhanced EPR effect, tumor delivery, anti-tumor effect or alike of the macromolecular drug, thereby showing an enhanced therapeutic effect of the macromolecular drug and a reduced side effect thereof.

In conclusion, according to the present invention, it is possible to significantly enhance the EPR effect, tumor delivery, antitumor effect, etc. of the macromolecular drug by administering it in combination with a specific EPR and/or antitumor effect enhancer.

BRIEF DESCRIPTION OF THE DRAWINGS

FIG. 1 shows the pH-dependent release of pirarubicin from polyhydroxypropylmethacrylamide (HPMA)-bound THP (P-THP).

FIG. 2 shows the effect of each reagent on water solubility of P-THP lyophilizate.

FIG. 3 illustrates the results for the stability of macromolecular carcinostatic agent P-THP (hydrazone bond) in various conditions of solutions, pH, and temperatures (A to G), which were analyzed by HPLC TSK3000 column. The vertical axis indicates the amount of pirarubicin (THP) generated by decomposition (absorption 488 nm). FIG. 3A shows the results for 3% arginine buffer, which were almost the same data as 1% arginine buffer. Further, FIGS. 3E to 3G show the results for 0.3 M arginine/arginine HCl buffer (pH 8.5), which were almost the same data as 3% sodium bicarbonate-sodium carbonate buffer (pH 8.5).

FIG. 4 shows the results for P-THP, which were analyzed by Sephacryl S-300. Elution: A is 0.1 M sodium bicarbonate (pH 8.2), B is 3% arginine (pH 8.5), C is PBS (0.01 M phosphate, 0.15 NaCl, pH 7.4) buffer. Both FIGS. 4A and B illustrate a sharp single peak showing a single molecular weight distribution. As shown in FIG. 4C, the release of THP was progressed in PBS. The parts indicated by the arrows on the peaks show the deviation from the uniformity of the peak (generation of decomposition products). It is understood that the width of the peak is wider than that of A or B.

FIG. 5 shows the enhancement of antitumor effect of P-THP on tumor (advanced breast cancer) by nitroglycerin.

FIG. 6 shows the enhancement of antitumor effect of P-THP on mice transplanted with S180 cells by nitroglycerin.

FIG. 7 shows the enhancement of antitumor effect of P-THP on azoxymethane-induced mice colon cancer by each EPR and/or antitumor effect enhancer.

DESCRIPTION OF EMBODIMENTS

The "macromolecular drug" in the present invention is not particularly limited, but includes conjugates or complexes formed from a drug such as a carcinostatic agent and a biocompatible polymer through a covalent or non-covalent bond.

The "drug" in the present invention is not particularly limited, but includes, for example, carcinostatic agents such as neocarzinostatin (NCS), pirarubicin (THP), and Zn-protoporphyrin (ZnPP), and fluorescent molecules such as rose bengal, methylene blue, acridine, acriflavine, acridine orange, and indocyanine green. Preferred are carcinostatic agents such as THP and ZnPP.

Examples of the biocompatible polymer include polyhydroxypropylmethacrylamide (HPMA) polymers, styrene-maleic acid copolymers (SMA), polyethylene glycols (PEG), and the like, preferably HPMA polymers and SMA.

The chemical bond connecting covalently the drug and the biocompatible polymer generally includes amides (R1-CO—NH—R2, wherein R1 and R2 are any groups, hereinafter the same shall apply), esters (R1-CO—O—R2), ethers (R1-O—R2), disulfide (R1-S—S—R2), hydrazones (R1-CO—NNH—R2), bonds through Schiff base (—C=NH—), hydrazone (hydrazine) bonds, and the like.

In particular, amides and esters have been widely used. Hydrazone bonds have also been widely used because they have a function of responding to a weak acid environment, thereby releasing drugs (F. Kratz et al, Drug Deliv. 6, 89-95 (1999); Bioorganic Med. Chem. Lett. 7, 617-622 (1997), etc.).

Further, even in amide bonds, when an amide bond is formed from the amino group of a drug (e.g., a carcinostatic compound) and R1 which is maleyl acid or aconityl acid, the drug is released at a weakly acidic pH or in the presence of 0.1% SDS (sodium dodecyl sulfate).

Examples of the conjugate/complex of the drug and the biocompatible polymer include those described in, e.g., WO 2003/018007, WO 2004/103409, WO 2006/112361, WO 2013/035750, WO 2015/076312, etc., such as P-THP, P-ZnPP, SMA-ZnPP, SMA-THP, PEG-THP, PEG-ZnPP, SMA-CDDP, etc. Preferred are those shown in Table 1 below.

TABLE 1

Examples of macromolecule-bound drugs used in intravenous injections in the present invention

| Macromolecule-bound drug | Macromolecule | Chemical bond | Original drug (active Pharmaceutical ingredient) |
|---|---|---|---|
| SMANCS | SMA[1)]-half-butyl ester | Amide (maleic acid amide) | Neocarzinostatin (NCS) |
| THP[2)] or HPMA polymer-THP | SMA or HPMA polymer | Amide | THP |
| THP or HPMA polymer-THP | SMA or HPMA polymer | Ester | THP |
| THP or HPMA polymer-THP | SMA or HPMA polymer | Hydrazone | THP |
| ZnPP[3)] or P[4)]-ZnPP | SMA or HPMA polymer | Amide | ZnPP |
| ZnPP | SMA or HPMA polymer | Ester | ZnPP |
| ZnPP | SMA or HPMA polymer | Hydrazone | ZnPP |
| Rose bengal nanoparticles | SMA or HPMA polymer | Non-covalent bond or Covalent bond | Rose bengal |
| Methylene blue nanoparticles | SMA or HPMA polymer | Non-covalent bond or Covalent bond | Methylene blue |
| Acridine nanoparticles | SMA or HPMA polymer | Non-covalent bond or Covalent bond | Acridine |

TABLE 1-continued

Examples of macromolecule-bound drugs used in intravenous injections in the present invention

| Macromolecule-bound drug | Macromolecule | Chemical bond | Original drug (active Pharmaceutical ingredient) |
|---|---|---|---|
| Acriflavine nanoparticles | SMA or HPMA polymer | Non-covalent bond or Covalent bond | Acriflavine |
| Acridine orange nanoparticles | SMA or HPMA polymer | Non-covalent bond or Covalent bond | Acridine orange |
| Indocyanine green nanoparticles | SMA or HPMA polymer | Non-covalent bond or Covalent bond | Indocyanine green |

[1] SMA: Styrene-maleic acid copolymer
[2] THP: Tetrapyranyl-doxorubicin (also referred to as "pirarubicin")
[3] ZnPP: Zn-cheleted protoporphyrin IX
[4] P: SMA or Hydroxypropylmethacrylamide (HPMA) polymer Specifically, the conjugate/complex of the macromolecular nature includes those represented by the following formulae.

(1) SMA-Bound THP (SMA-THP Complex, Amide Bond)

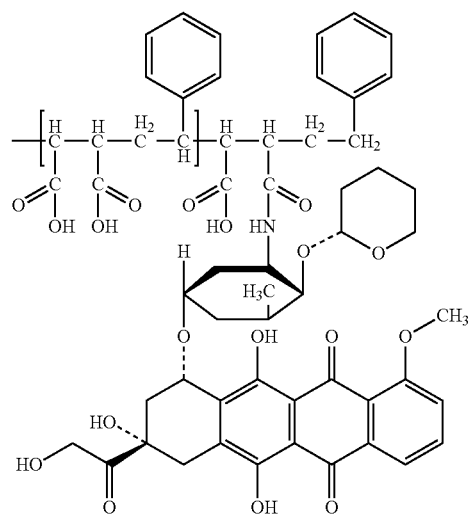

[Formula 1]

(2) HPMA Polymer-THP (Pirarubicin) (Referred to as "P-THP") (Hydrazone Bond)

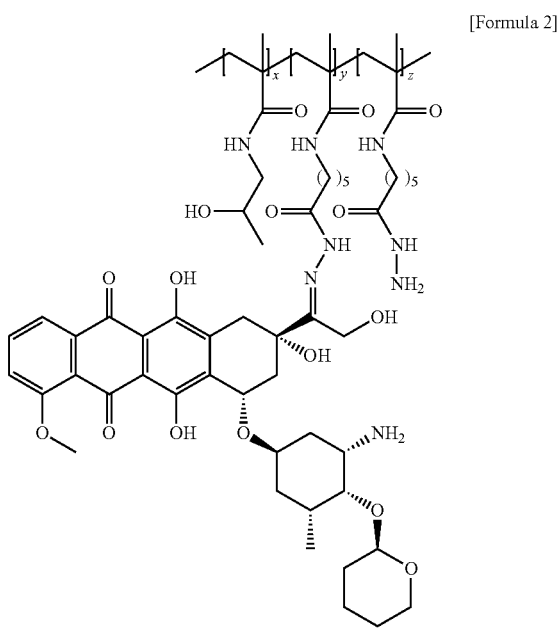

[Formula 2]

(3) SMA-Copolymer-THP (Hydrazone Bond)

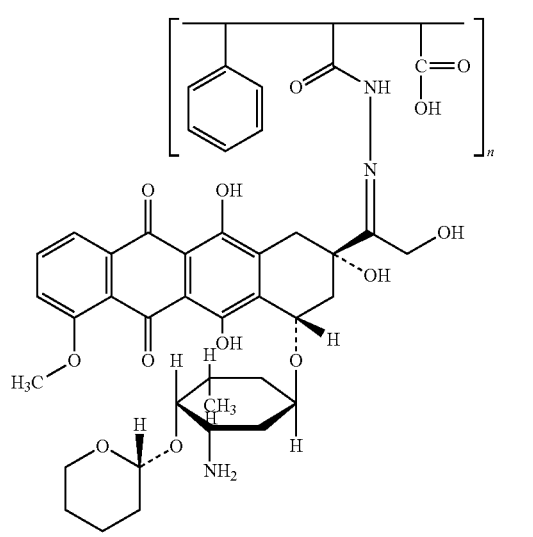

[Formula 3]

(4) HPMA-ZnPP
[Formula 4]
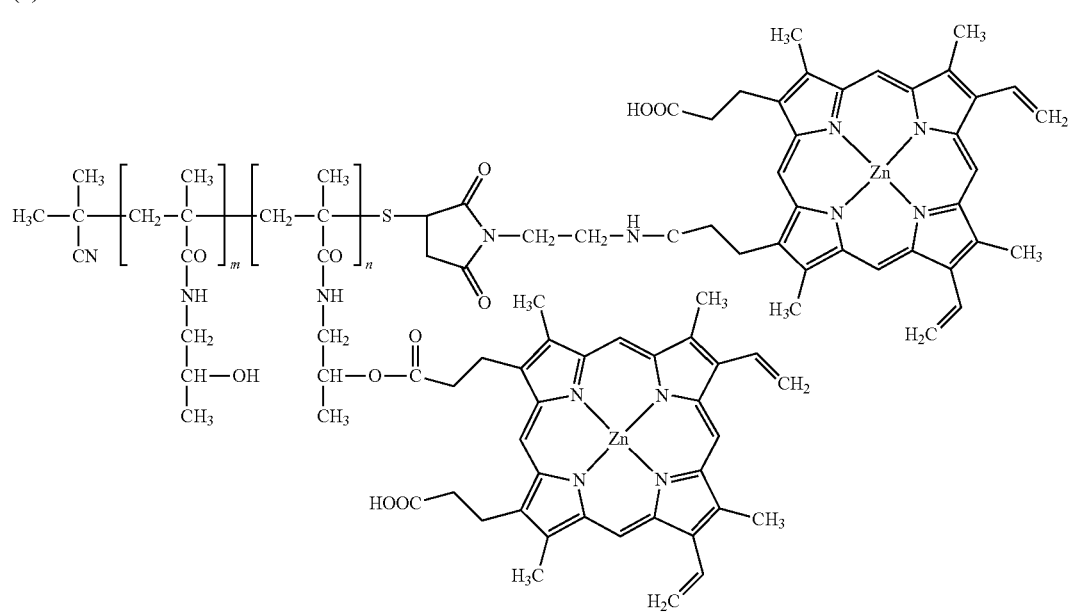
(5) Poly-HPMA-ZnPP
[Formula 5]
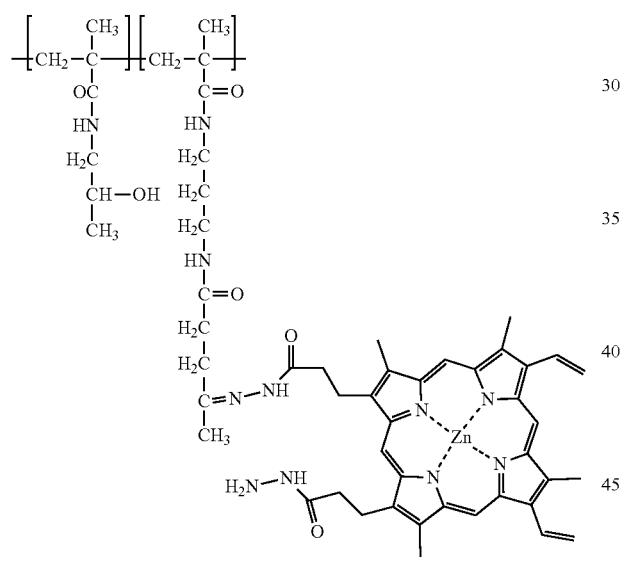
(6) SMA-ZnPP
[Formula 6]
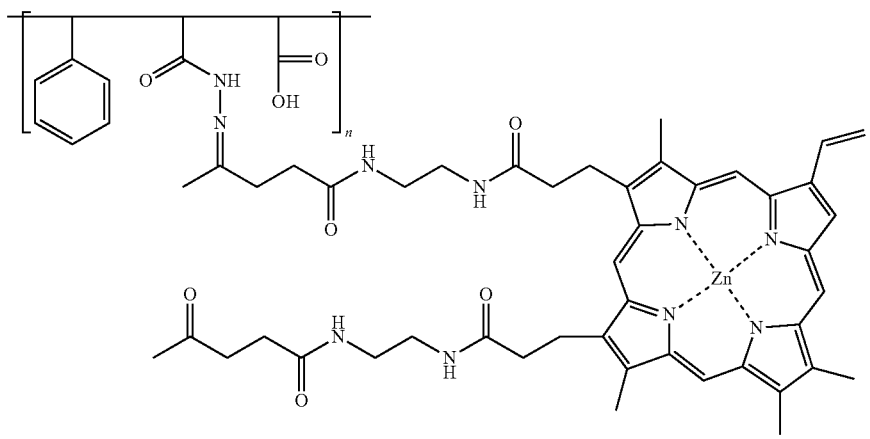

As the conjugates (1) and (2), preferred are those satisfying one of the following properties, and particularly preferred are those satisfying all the following properties:
Molecular weight (MW): >40 KDa
Size/DLS: up to 50 nm
Surface charge: −28 mV
THP load: 1 to 50% (w/w), preferably 10 (w/w)
Cellular uptake: >10 to 100 times compared to Dox
Plasma $t_{1/2}$: 100 to 200 times compared to THP
$DL_{50}$: 100 to 200 mg/kg (up to 10 times better compared to original drug: that is, lower toxicity)
Tumor/blood: >110 to 200 times compared to THP
In vitro cytotoxicity: 0.5 to 50% compared to free THP The in vivo stability of the conjugates varies greatly depending on the types of chemical bonds and tends to decompose in the order of ether, amide, ester, and hydrazine bonds in the presence of serum components. On the other hand, at lower pH, hydrazone bond is most susceptible to cleavage.

Also, the cleavage of ester bond by animal sera varies depending on differences in animals and becomes slower in the order: mouse, rat>rabbit>human. Further, human colon cancer homogenates cleave ester bond faster than normal tissue homogenate and the rate of cleavage thereof found slower in the order: ester>amide>ether (Tsukigawa et al, Eur. J. Pharm. Biopharm 89, 259-270 (2015)).

The above conjugates (1) to (3) are those obtained by forming an ester bond, an amide bond or a hydrazone bond, which is formed from an amino group, a carboxyl group or a ketone group present in a THP molecule and a maleic anhydride group or a carboxyl group of SMA or a hydroxyl group of HPMA, alternatively via using a linker such as a hydrazine shown in WO 2015/076312.

Such conjugates can be prepared by the methods described in, for example, WO 2013/035750, WO 2015/076312, H. Nakamura et al, J. Control Release (2014) 174, p 81-87, and H. Nakamura et al, J. Control Release (2013) 165, p 191-198.

The "dissolution-enhancing and/or stabilizing agent" used in the present invention is not particularly limited as long as it can improve the solubility and/or stability of the macromolecular drug in an aqueous solvent, but includes, for example, the followings:
(1) proteins: human serum albumin, transferrin, immunoglobulin, soluble gelatin, succinylated (acylated) gelatin, modified gelatin, etc.
(2) synthetic polymers: polyethylene glycol (PEG), polypropylene glycol, vinyl alcohol, polyvinyl alcohol, polyvinyl pyrrolidone, hydroxypropyl methacrylamide (HPMA) polymer, etc.
(3) sugars or sugar alcohols: methyl cellosolve, glycyrrhizin, glucose, mannitol, maltose, sorbitol, sorbic acid, lactose, trehalose, dextran, cyclodextrin, glycerin (glycerol), solubilized starch, etc.
(4) inorganic salts: sodium bicarbonate, etc.,
(5) amino acids: glycine, glycylglycine, alanine, serine, threonine, glutathione, cysteine, arginine (L-arginine), lysine, histidine, ornithine, citrulline, etc.
(6) phospholipids: lecithin, etc.
(7) aliphatic alcohols: cetyl alcohol, etc.
(8) medium-chain fatty acids: fatty acids having 5 to 10 carbon atoms such as octylic acid, etc.
(9) mucopolysaccharides: hyaluronic acid, chondroitin sulfate, etc.

These may be one that has been approved by the Japanese Pharmacopoeia, or unapproved ones. These may be used in combination of two or more.

In the pharmaceutical composition of the present invention, amino acids (arginine, glycine, citrulline, etc.), sodium bicarbonate, PEG, and the like are particularly preferable in view of the improvement of solubility, the improvement of stability, the suppression of decomposition, the enhancement of EPR effect, the tumor delivery, hence the antitumor effect, and the like of the macromolecule-bound drugs.

The amount of the dissolution accelerating and/or stabilizer is usually 0.01 to 50 parts by weight, preferably 1 to 10 parts by weight, relative to 1 part by weight of the macromolecular drug.

The "aqueous solvent" used in the present invention is not particularly limited as long as it can be used for an injection and the like, but includes, for example, water such as distilled water, deionized water, purified water, sterile purified water, water for an injection, and these water with various additives such as saline (5%), 5% aqueous sodium bicarbonate, Ringer solution, and the like. Moreover, its pH is generally not more than 9.0, preferably, for example, 7.8 to 8.7, 7.0 to 8.0, and the like. Osmotic pressure is not particularly limited.

A drug linked to a polymer via a hydrazone bond, a maleyl amide bond, or the like, such as the conjugates (1) and (2), can be broken away and released from the polymer when a solution is acidic pH (FIG. 1). When the pharmaceutical composition of the present invention is a liquid preparation, therefore, the pH of the liquid preparation is preferably not less than 6.0, more preferably, for example, 7.5 to 9.0, 7.8 to 8.7, 7.0 to 8.0, and the like.

The pharmaceutical composition of the present invention can be prepared by conventional methods in the field of formulation. For example, the pharmaceutical composition of the present invention which is a liquid preparation such as injection, etc. can be produced by dissolving the macromolecular drug and the dissolution-enhancing and/or stabilizing agent into 10 ml to 1 l of an aqueous solvent (aqueous solution) in a ratio of, for example, 0.01 g to 50 g (preferably 0.1 g to 10 g) of the dissolution-enhancing and/or stabilizing agent to 1 g of the macromolecular drug.

The concentrations of the macromolecular drug and the dissolution-enhancing and/or stabilizing agent may be appropriately set in accordance with the desired effect and the administration method (e.g., intravenous injection, intravenous slow infusion, etc.). For example, the concentration of the macromolecular drug may be 0.01 to 60% (w/v), particularly 0.1 to 20% (w/v). Further, the concentration of the dissolution-enhancing and/or stabilizing agent may be, for example, 0.1 to 10% (w/v), particularly 1 to 10% (w/v).

The pharmaceutical composition of the present invention may not contain any aqueous solvent. That is, it includes a pharmaceutical composition comprising the macromolecular drug and the dissolution-enhancing and/or stabilizing agent, in addition to a pharmaceutical composition comprising the macromolecular drug, the dissolution-enhancing and/or stabilizing agent and the aqueous solvent.

The pharmaceutical composition of the present invention comprising the macromolecular drug and the dissolution-enhancing and/or stabilizing agent can be prepared by conventional methods in the field of formulation. For example, it can be prepared by simply mixing the dissolution enhancer and/or stabilizer with the macromolecular drug.

Also, the pharmaceutical composition of the present invention can be prepared by lyophilizing the above liquid preparation in conventional manners. In this case, it is possible to achieve a stable and prolonged storage of the pharmaceutical composition of the present invention as a solid preparation (e.g. solid form injection).

Further, the macromolecular drug and the dissolution-enhancing and/or stabilizing agent are individually formulated into a single solid preparation or are formulated together into a solid preparation of the mixture thereof. Various additives used in aqueous solvents may be previously mixed with these solid preparations. The solid preparations may be a kit comprising a plurality of preparations.

The above solid preparation may be dissolved in any volume of distilled water when used. It may be dissolved in a small amount (about 10 ml) of distilled water to form an injection, or even more amount (10 ml to 500 ml, preferably 200 to 300 ml) of distilled water to form an intravenous infusion solution.

The pharmaceutical composition of the present invention is preferably for use as injection. The "injection" in the present invention includes aqueous injection, suspendable injection, emulsifiable injection, solid injection, intravenous infusion, infusion preparation, and the like. In the present invention, preferred is an injection for intravenous injection or infusion.

Further, in the pharmaceutical composition of the present invention, the dissolution-enhancing and/or stabilizing agent can be administered with the macromolecular drug simultaneously or separately, as a single formulation or separate formulations, in the same or different routes, to a patient (mammals such as human). For example, a formulation containing the macromolecular drug can be intravenously administered: Also, the dissolution-enhancing and/or stabilizing agent can be intraperitoneally administered.

The pharmaceutical composition of the present invention may contain an EPR and/or antitumor effect enhancer, in addition to or separately from the dissolution-enhancing and/or stabilizing agent. The EPR and/or antitumor effect enhancer is not particularly limited as long as an agent capable of potentiating the EPR effect and/or anti-tumor effect, but includes, for example, (a) nitroglycerin (NG), (b) ISDN (isosorbitedinitrate), (c) nitro group-containing antihypertensive agents, such as perdipine, (d) Sultan drugs, (e) angiotensin converting enzyme inhibitors (ACE inhibitors), such as Verapamil® (enalapril), (f) vascular hyperpermeability factors, such as styrene-maleic acid copolymer micelle formulations of a carbon monoxide (CO) releasing agent ruthenium carbonate (CORM2), developed by the present inventors (see J. Fang et al., J. Control. Release (2014) 187, p. 14-21), (g) hemin or hemin derivatives capable of inducing heme-oxygenaze-1 (HO-1), which is one of CO-synthesis enzymes (e.g., PEG bound-hemin), (h) beraprost Na, which is a stabilized formulation of a derivative of prostaglandin $I_2$, (i) substrates for NO (nitric oxide) synthase (nitric oxide synthase, NOS), e.g., arginine (L-arginine), and citrulline, (j) NO releasing agents, e.g., nitroprusside, nitrous acid, nitroamyl alcohol, S-nitroso-glutathione, S-nitroglutathione, and S-nitroso-cysteine, (k) urea derivatives, e.g., hydroxyurea, and nitrosourea, and the like.

Preferred are ISDN, nitroglycerin, perdipine, ACE inhibitors, nitroprusside, nitroso amino alcohol, Rozarutan antihypertensive agents, arginine, hydroxyurea, nitrosourea, and the like, and particularly preferred are nitroglycerin, arginine, hydroxyurea, and the like.

Regarding the agents of the above (i), arginine is the substrate for NO synthase (NOS) and can generate NO in tumor site to enhance the EPR effect by vasodilator action. The concomitant use of arginine can keep a continuous production of NO in tumor site to continuously increase the EPR effect as with NG mentioned above. Citrulline is useful as a raw material for NO generation like arginine, because it becomes argininosuccinate in arginine synthesis cycle and then it becomes arginine.

Further, regarding the agents of the above (j), nitrite ion is converted to NO by nitrite reductase in tumor site, which is under a lower oxygen partial pressure, resulting in the enhancement of EPR effect (T. Seki et al, Cancer Science (2009) 100, 2426-2430).

The amount of the EPR and/or antitumor effect enhancer in the pharmaceutical composition of the present invention is not particularly limited as long as the desired effect can be obtained, but can be, for example, 1 µg to 100 mg/vial. Further, when the pharmaceutical composition of the present invention is a liquid preparation, the concentration of the agent may be, for example, 0.1 to 30 (w/v), particularly 1 to 10% (w/v).

The EPR and/or antitumor effect enhancer may be mixed at any stage of the preparation process of the pharmaceutical composition of the present invention. For example, it may be pre-dissolved in the aqueous solvent, may be pre-mixed with the macromolecular drug and/or the dissolution-enhancing and/or stabilizing agent, and also may be added to the aqueous solvent simultaneously with the macromolecular drug and/or the dissolution-enhancing and/or stabilizing agent. It is also preferable to add it into an infusion solution (drug) when infused into a patient.

Further, in the pharmaceutical composition of the present invention, the EPR and/or antitumor effect enhancer can be administered with the macromolecular drug simultaneously or separately, as a single formulation or separate formulations, in the same or separate routes, to a patient (mammals such as human). For example, a formulation containing the macromolecular drug can be orally administered, while the EPR and/or antitumor effect enhancer can be administered by application.

In the pharmaceutical composition of the present invention, arginine can be used both as the dissolution-enhancing and/or stabilizing agent and as the EPR and/or antitumor effect enhancer. When the pharmaceutical composition of the present invention is a liquid preparation containing arginine, the concentration of arginine is usually 0.01 to 30% (w/v), preferably 0.1 to 10% (w/v), and the pH of the liquid preparation is usually 7.0 to 9.0, preferably, for example, 7.8 to 9.5, 8.0 to 9.0, 8.2 to around 8.8, 7.0 to 8.0, or the like. To the liquid preparation may be added glucose or mannitol in an amount of 0.1 to 10% (w/v), preferably around 8% (w/v), and also may be added a suitable amount (1 µg to 100 mg/vial) of ISDN, nitroglycerin or perdipine.

The pharmaceutical composition of the present invention may optionally contain various additives for pharmaceutical preparations, such as pH adjusting agents, dispersing agents, wetting agents, stabilizers, preservatives, suspending agents, surfactants, and the like. The usage of them can be determined by conventional methods.

EXAMPLES

Hereinafter, the present invention will be described in more detail with reference to examples, test examples, etc., but the present invention is not limited to the following examples.

Test Example 1

Enhancement of Tumor Delivery of P-THP by Concomitant Use of the EPR and/or Antitumor Effect Enhancer Sample: A freeze-dried product prepared from an aqueous solution of polyhydroxypropyl methacrylamide-bound pirarubicin (hydrazone bond) (P-THP) (apparent molecular weight is 40,000 or more) was used as a sample.

Method: In 1 ml of saline (0.01 M phosphate, 0.15 M NaCl, pH 7.4) were dissolved 10 mg of each sample (10 mg/ml) and the predetermined amount of each test reagent shown in Table 2. Then, 0.1 ml of each obtained solution and 0.1 ml of an aqueous solution (10 mg/ml) of Evans blue were intravenously administered to S-180 mice (tumor model) The tumor size of the mice was a diameter of 5 to 7 mm. The next day, each mouse was dissected and solid tumors were taken out therefrom. Evans blue was extracted by a conventional method and the leaked Evans blue was quantified by absorption of 560 nm (see Non-Patent Document 1). The results are shown in Table 2.

TABLE 2

Improvement of tumor delivery by concomitant use of the EPR and/or antitumor effect enhancer
(Values are relative accumulation amounts of Evans blue-albumin after Bolus administration: Drug P-THP*)

| | Test reagent | Tumor | Plasma | Liver | Lung | Heart | Kidney |
|---|---|---|---|---|---|---|---|
| Comparative Example 1 | No drug (Control) | 100 | 76.5 | 21.0 | 14.0 | 5.5 | 25.5 |
| Comparative Example 2 | Nicardipine (1 µg) | 100 | 88.0 | 21.0 | 17.0 | 5.0 | 23.1 |
| Example 1 | Azilsartan (2 g) | 139 | 71.0 | 16.5 | 19.5 | 6.5 | 24.0 |
| Example 2 | Arginine | | | | | | |
| 2-1 | (5%) | 133 | 68.0 | 23.0 | 13.0 | 7.0 | 25.0 |
| 2-2 | (10%) | 148 | 20.0 | 21.5 | 12.5 | — | — |
| Example 3 | Nitroglycerin | | | | | | |
| 3-1 | (10 µg/ml) | 130 | 79.0 | 23.0 | 16.0 | 9.0 | 19.0 |
| 3-2 | (20 µg/ml) | 145 | 75.0 | 22.1 | 17.0 | — | — |

*polyhydroxypropyl methacrylamide-bound pirarubicin (hydrazone bond)

As shown in Table 2, all of azilsartan, arginine and nitroglycerin showed a significantly enhanced effect in 30% or more.

Test Example 2

Effects of Each Reagent on the Solubility of P-THP Lyophilizate

Sample: A P-THP (containing hydrazone bond) was prepared according to the report by Nakamura, et al. (J. Controlled Release, 174, 81-87 (2014)), and then 500 mg of the product was dissolved in distilled water and freeze-dried by a conventional method. The lyophilized powder was used as a sample.

Method: 10 mg of the above sample powder was taken into each tube, and then 10 ml of a solution containing the predetermined amount of each test compound (from arginine to glycine) for promoting solubilization shown in Table 3 below and FIG. 2. These aqueous solutions were either 1-10%, 0.3 M (mol/l) arginine/arginine HCl buffers or 1-5% sodium bicarbonate/sodium carbonate buffers, both of which were adjusted to pH 8.5. Then, the solubility of the sample was visually determined under shaking. The time until complete dissolution judged by visual observation was measured with a stopwatch. The results are shown in Table 3 below and FIG. 2.

TABLE 3

Effects of each reagent on the solubility of P-THP lyophilizate (pH 8.5)

| | Test reagent | Dissolution time (min) |
|---|---|---|
| Comparative Example 3 | Control (P-THP only) | 1.47 |
| Example 4 | Arginine | |
| 4-1 | (1%) | 0.32 |
| 4-2 | (3%) | 0.23 |
| 4-3 | (5%) | 0.80 |
| 4-4 | (10%) | 0.52 |
| Example 5 | Sodium bicarbonate | |
| 5-1 | (1%) | 0.32 |
| 5-2 | (3%) | 0.25 |
| 5-3 | (5%) | 0.72 |
| Example 6 | Mannitol | 0.3M arginine buffer |
| 6-1 | (0.3%) | 0.60 |
| 6-2 | (1%) | 0.58 |
| 6-3 | (3%) | 0.18 |
| Example 7 | PEG | Id. |
| 7-1 | (1%) | 0.47 |
| 7-2 | (3%) | 0.32 |
| Example 8 | Glycine | Id. |
| 8-1 | (0.3%) | 0.82 |
| 8-2 | (1%) | 0.48 |
| 8-3 | (3%) | 0.38 |

Test Example 3

Dissolution Time of P-THP Dry Powder Formulation in Each Aqueous Solution

Sample: A P-THP (hydrazone bond) was prepared according to the report by Nakamura, et al. (J. Controlled Release, 174, 81-87 (2014)), and then the solvent was evaporated to obtain a dry powder product (not freeze-dried product). The dry powder product was used as a sample.

Method: 10 mg of the above sample (dried product of P-THP) was taken into each tube, and then a solution containing the predetermined amount of arginine, sodium bicarbonate, mannitol, PEG, or glycine (10 ml, pH 8.0 to 9.0) shown in Table 4 was added thereto. As with Table 3 except for control, 0.3 M arginine/arginine HCl buffer or 3% sodium bicarbonate/sodium carbonate buffer (pH 8.0-9.0) was used as an aqueous solution.

Then, the complete dissolution time of P-THP was measured with a stopwatch according to the method shown in Test Example 2. The results are shown in Table 4 below, along with each solution used in this test, its concentration and its pH.

TABLE 4

Dissolution time of P-THP dry powder product in aqueous solutions (10 mg/ml)

| | Test drugs | pH | Dissolution time (min) |
|---|---|---|---|
| Comparative Example 3 | Control (Distillated water) | 7.0 | 3.4 |
| Comparative Example 4 | Control (Saline) 0.01M phosphate buffered 0.15M NaCl | 7.4 | 4.5 |
| Example 9 | Arginine | | |
| 9-1 | (1%) | 7.0 | 2.0 |
| 9-2 | (1%) | 8.0 | 2.7 |
| 9-3 | (1%) | 8.2 | 2.4 |
| 9-4 | (1%) | 8.5 | 2.3 |
| 9-5 | (1%) | 9.0 | 2.5 |

TABLE 4-continued

Dissolution time of P-THP dry powder product in aqueous solutions (10 mg/ml)

|  | Test drugs | pH | Dissolution time (min) |
|---|---|---|---|
| Example 10 | Arginine |  |  |
| 10-1 | (3%) | 7.0 | 2.5 |
| 10-2 | (3%) | 8.0 | 3.2 |
| 10-3 | (3%) | 8.2 | 2.0 |
| 10-4 | (3%) | 8.5 | 2.1 |
| 10-5 | (3%) | 9.0 | 2.2 |
| Example 11 | Arginine |  |  |
| 11-1 | (10%) | 7.0 | 1.8 |
| 11-2 | (10%) | 8.0 | 2.1 |
| 11-3 | (10%) | 8.2 | 2.0 |
| 11-4 | (10%) | 8.5 | 2.1 |
| 11-5 | (10%) | 9.0 | 2.5 |
| Example 12 | Sodium bicarbonate |  |  |
| 12-1 | (1%) | 7.0 | 2.0 |
| 12-2 | (1%) | 8.0 | 2.1 |
| 12-3 | (1%) | 8.2 | 2.0 |
| 12-4 | (1%) | 8.5 | 2.0 |
| 12-5 | (1%) | 9.0 | 2.1 |
| Example 13 | Sodium bicarbonate |  |  |
| 13-1 | (5%) | 7.0 | 3.3 |
| 13-2 | (5%) | 8.0 | 3.0 |
| 13-3 | (5%) | 8.2 | 2.1 |
| 13-4 | (5%) | 8.5 | 1.5 |
| 13-5 | (5%) | 9.0 | 2.0 |
| Example 14 | Mannitol | 0.3M arginine buffer |  |
| 14-1 | (3%) | 7.0 | 1.5 |
| 14-2 | (3%) | 8.0 | 1.5 |
| 14-3 | (3%) | 8.2 | 1.2 |
| 14-4 | (3%) | 8.5 | 1.1 |
| 14-5 | (3%) | 9.0 | 1.2 |
| Example 15 | PEG | 3% sodium bicarbonate buffer |  |
| 15-1 | (3%) | 7.0 | 2.5 |
| 15-2 | (3%) | 8.0 | 2.2 |
| 15-3 | (3%) | 8.2 | 2.1 |
| 15-4 | (3%) | 8.5 | 2.0 |
| 15-5 | (3%) | 9.0 | 2.1 |

As shown in Table 4, the water-solubility of P-THP was greatly improved by the use of the predetermined dissolution-enhancing and/or stabilizing agent such as arginine.

Test Example 4

Sample: A lyophilized product of P-THP was prepared in the same manner as in Test Example 2 and used as a sample.

Method: The sample (lyophilized product of P-THP) was dissolved in each solution shown in Table 5 below, and the obtained solution was incubated under each condition shown in Table 5 below. In this test, 0.1 M acetic acid/sodium acetate buffer (pH 6.0), 0.1 M phosphate buffer (pH 7.0, 8.2, and 8.6), 0.3 M arginine/arginine HCl buffer or 3% sodium bicarbonate/sodium carbonate buffer (pH 8.5) was used as an aqueous solution.

Then, the decomposition product, i.e. free pirarubicin (THP), was separated by HPLC (High Performance Liquid Chromatography) (column: JSK Gel SW3000, Detection: Absorbance 488 nm, Elution: a mixed solution of 80% methanol and 20% 0.1 M sodium acetate at pH 7.0) and quantified by absorbance at 488 nm. From the results, the reduced amount of the original P-THP was calculated and plotted for the stability of P-THP in each solution. The results are shown in Table 5 and FIGS. 3A to G.

TABLE 5

| FIG. |  | Aqueous solution | pH | Incubation results |
|---|---|---|---|---|
| A, B | Example 16 | 3% arginine buffer |  |  |
|  | 16-1 |  | 7.0 | 80% decomposition for 27 days at 25° C. (B) |
|  | 16-2 |  | 8.0 | 75% stable for 27 days at 25° C. (B) |
|  | 16-3 |  | 8.5 |  |
|  | 16-4 |  | 9.0 |  |
| C, D | Comparative Example 6 | 0.1M phosphate buffer |  |  |
|  | 6-1 |  | 7.0 | 80% decomposition for 5 days at 25° C. (D) |
|  | 6-2 |  | 8.2 | 30-40% decomposition for 5 days at 25° C. (D) |
|  | 6-3 |  | 8.6 |  |
| E | Comparative Example 7 | Absence of both NaCl and SDS (sodium dodecyl sulfate) | 6.0 | 30% or more decomposition for 24 hours at 25° C. |
|  | Example 17 |  | 8.5 | Almost stable |
| F | Comparative Example 8 | 0.1% SDS only | 6.0 | 30% or more decomposition for 24 days at 25° C. in the presence of 0.1% SDS |
|  | Example 18 |  | 8.5 | Almost stable |
| G | Comparative Example 9 | 0.5M NaCl only | 6.0 | 20-40% decomposition for 24 days at 25° C. in the presence of 0.5M NaCl |
|  | Example 19 |  | 8.5 | Almost stable |

FIG. 3A shows the results for 3% arginine buffer. Almost the same results as them were obtained for 1% arginine buffer. FIGS. 3E to 3G show the results for 0.3 M arginine/arginine HCl buffer (pH 8.5). Almost the same results as them were obtained for 3% sodium bicarbonate/sodium carbonate buffer (pH 8.5). From these results, it was found that P-THP exhibits the best stability in the vicinity of pH 8.5 both in arginine buffers and sodium bicarbonate buffers.

Test Example 5

Sample: A P-THP was prepared in the same manner as in Test Example 2 and used as a sample.

Method: The P-THP was dissolved in each of Solution A (Example 20: 0.1 M aqueous solution of sodium bicarbonate, pH 8.2), Solution B (Example 21: 3% arginine buffer, pH 8.5), and Solution C (Comparative Example 10: PBS (0.01 M phosphate, 0.15 M NaCl), pH 7.4) and left at room temperature for 24 hours. It was then subjected to column chromatography (φ1.8×70 cm) of Sephacryl S300. The column was eluted with the same solution, respectively.

Then, free pirarubicin (THP) liberated under the above condition was determined by using HPLC (High Performance Liquid Chromatography) JSK Gel SW3000 with eluting a mixed solution of 80% methanol and 20% 0.1 M sodium acetate at pH 7.0 and measuring absorbance at 488 nm. The results are shown in FIG. 4.

As shown in FIGS. 4A to 4C, both Solutions A and B showed a sharp single clean peak. In Solution C, decomposition products of THP were found as indicated by the arrows, and the uniformity of the peak was not observed. The peak shown in Solution C was wider than those shown in Solutions A and B. It is thus understood that an arginine buffer and a sodium bicarbonate buffer are superior to PBS.

Test Example 6

When 1 ml of a corn oil solution of a chemical carcinogen dimethyl benzanthracene (DMBA) (10 mg/ml) is orally administered to SD rats (250 to 300 g/animal, 5 weeks old) by using a sonde, breast cancer occurs 12 to 14 weeks later.

To SD rats (5 animals/group) with breast cancer generated by the above method, polyhydroxypropylmethacrylamide-bound pirarubicin (P-THP) alone was intravenously (i.v.) administered (P-THP group), or in addition to the i.v. administration of P-THP, nitroglycerin (0.2 mg/mouse) was applied (P-THP+NG group). The above administration of drugs was performed four times in total during the test period. The dose of P-THP was set to 5 mg/kg in each case.

During the period of time from 0 day to 140 days after the administration of these drugs, the tumor volume ($mm^3$) was measured (FIG. 5). As a result, the group of nitroglycerin application in combination with P-THP administration showed a significantly higher tumor-suppressing effect compared to the group of P-THP alone.

Test Example 7

When approximately $10^6$ cells of S-180 mouse sarcoma, which have been intraperitoneally implanted into ddY mice and passaged by mouse ascites every 10 days, are subcutaneously transplanted to 6-week-old ddY mice, tumor having a diameter of 5-6 mm occurs around 10 days later.

In above mice S-180 mouse sarcoma grew for experiment for the P-THP (15 mg) alone given intravenously (i.v.) (P-THP group), or in addition to the i.v. administration of P-THP, nitroglycerin (0.1 mg/mouse) was applied (P-THP+NG group).

During the period of time from 0 day to 40 days after the administration of these drugs, the tumor volume ($mm^3$) was measured (FIG. 6). As a result, the group of nitroglycerin application in combination with P-THP administration showed a significantly higher tumor-suppressing effect compared to the group of P-THP alone.

Test Example 8

To mouse models bearing colon tumor which was generated 100 days after the intraperitoneal (i.p.) administration of azoxymethane (AZM) (10 mg/kg) and followed by oral (p.o.) administration of Na dextran sulfate (2%, 0.2 to 1.0 ml) for 1 week, 15 mg/kg of P-THP was i.v. administered once (P-THP group); in combination with the i.v. administration of P-THP (15 mg), a nitroglycerin ointment (0.1 mg/mouse) was applied (P-THP+NG group); in addition to the i.v. administration of P-THP (15 mg), L-arginine (10 to 50 mg/mouse) was i.p. administered (P-THP+Arg group); or in combination with the i.v. administration of P-THP (15 mg), hydroxyurea (HU)(1.5 mg/mouse) was i.p. administered (P-THP+HU group).

After administration of these drugs, the sum of the diameter of all colon tumor nodules (mm) was calculated (FIG. 7). The diameter of the tumor nodules referred to herein is the value obtained by intravenously injecting rhodamine-labeled BSA (bovine serum albumin) into mice (1 mg/mouse), and the next day, excising the large intestines of the mice under urethane anesthesia, and then measuring the size of fluorescent spot of tumor nodules by an IVIS system with a caliper.

As a result, all of P-THP+NG group, P-THP+Arg group and P-THP+HU group showed a significantly higher tumor-suppressing effect compared to P-THP group.

The invention claimed is:

1. A pharmaceutical composition comprising a macromolecular drug, a dissolution-enhancing and/or stabilizing agent, and an aqueous solvent,
   wherein the macromolecular drug is a polyhydroxypropylmethacrylamide polymer-bound pirarubicin, and
   the dissolution-enhancing and/or stabilizing agent is at least one selected from the group consisting of arginine and sodium bicarbonate.

2. The pharmaceutical composition according to claim 1, which has a pH of 7.0 to 8.0.

3. The pharmaceutical composition according to claim 1, which is a liquid injection formulation.

4. The pharmaceutical composition according to claim 1, wherein the dissolution-enhancing and/or stabilizing agent is.

5. The pharmaceutical composition according to claim 1, which further comprises an enhanced permeability and retention effect and/or antitumor effect enhancer.

6. The pharmaceutical composition according to claim 1, which is for carcinostatic or anti-tumor effect.

7. A method for producing the pharmaceutical composition according to claim 1, which comprises mixing the macromolecular drug, the dissolution-enhancing and/or stabilizing agent, and the aqueous solvent.

8. A pharmaceutical composition comprising a macromolecular drug, and a dissolution-enhancing and/or stabilizing agent,
   wherein the macromolecular drug
   is a polyhydroxypropylmethacrylamide polymer-bound pirarubicin, and
   the dissolution-enhancing and/or stabilizing agent is at least one selected from the group consisting of arginine and sodium bicarbonate.

9. The pharmaceutical composition of claim 8, which further comprises an enhanced permeability and retention effect and/or antitumor effect enhancer.

10. A method for enhancing dissolution and/or stabilizing a macromolecular drug,
- wherein the macromolecular drug
  is a polyhydroxypropylmethacrylamide polymer-bound pirarubicin,
- which comprises mixing the macromolecular drug with at least one dissolution-enhancing and/or stabilizing agent selected from the group consisting of arginine and sodium bicarbonate, and an aqueous solvent.

\* \* \* \* \*